United States Patent
Eizenhöfer

[11] Patent Number: 5,941,838
[45] Date of Patent: Aug. 24, 1999

[54] SHOCK WAVE SOURCE BASED ON THE ELECTROMAGNETIC PRINCIPLE

[75] Inventor: Harald Eizenhöfer, Seefeld, Germany

[73] Assignee: Dornier Medizintechnik GmbH, Wessling, Germany

[21] Appl. No.: 09/153,200

[22] Filed: Sep. 15, 1998

Related U.S. Application Data

[63] Continuation-in-part of application No. 08/873,428, Jun. 12, 1997, abandoned.

[30] Foreign Application Priority Data

Jul. 26, 1996 [DE] Germany ............... 196 30 180

[51] Int. Cl.[6] .................................. A61B 17/22
[52] U.S. Cl. ................... 601/2; 601/4; 367/175
[58] Field of Search ............. 601/2–4; 600/439; 367/175; 181/148

[56] References Cited

FOREIGN PATENT DOCUMENTS

| | | |
|---|---|---|
| 0 298 334 A1 | 6/1988 | European Pat. Off. . |
| 33 12 014 A1 | 10/1984 | Germany . |
| 36 34 378 A1 | 4/1988 | Germany . |
| 34 43 295 | 3/1989 | Germany . |

*Primary Examiner*—Ruth S. Smith
*Attorney, Agent, or Firm*—McGlew and Tuttle, P.C.

[57] ABSTRACT

Shock wave source based on the electromagnetic principle with defined focusing, with an electrically conductive, three-dimensionally curved membrane, with a coil, which is located adjacent thereto and to which current pulses can be admitted. A switchable electric connection is provided between the coil and a power supply unit. A housing is provided accommodating the membrane and the coil embedded in a coil form, between which housing and the membrane the coil form is located. A transmission medium is provided adjacent to the membrane and exerts pressure on the membrane. The coil form is made deformable and elastically compressible and is installed in the compressed state. The installed amount of the transmission medium remains unaffected during the operating state after the assembly.

20 Claims, 1 Drawing Sheet

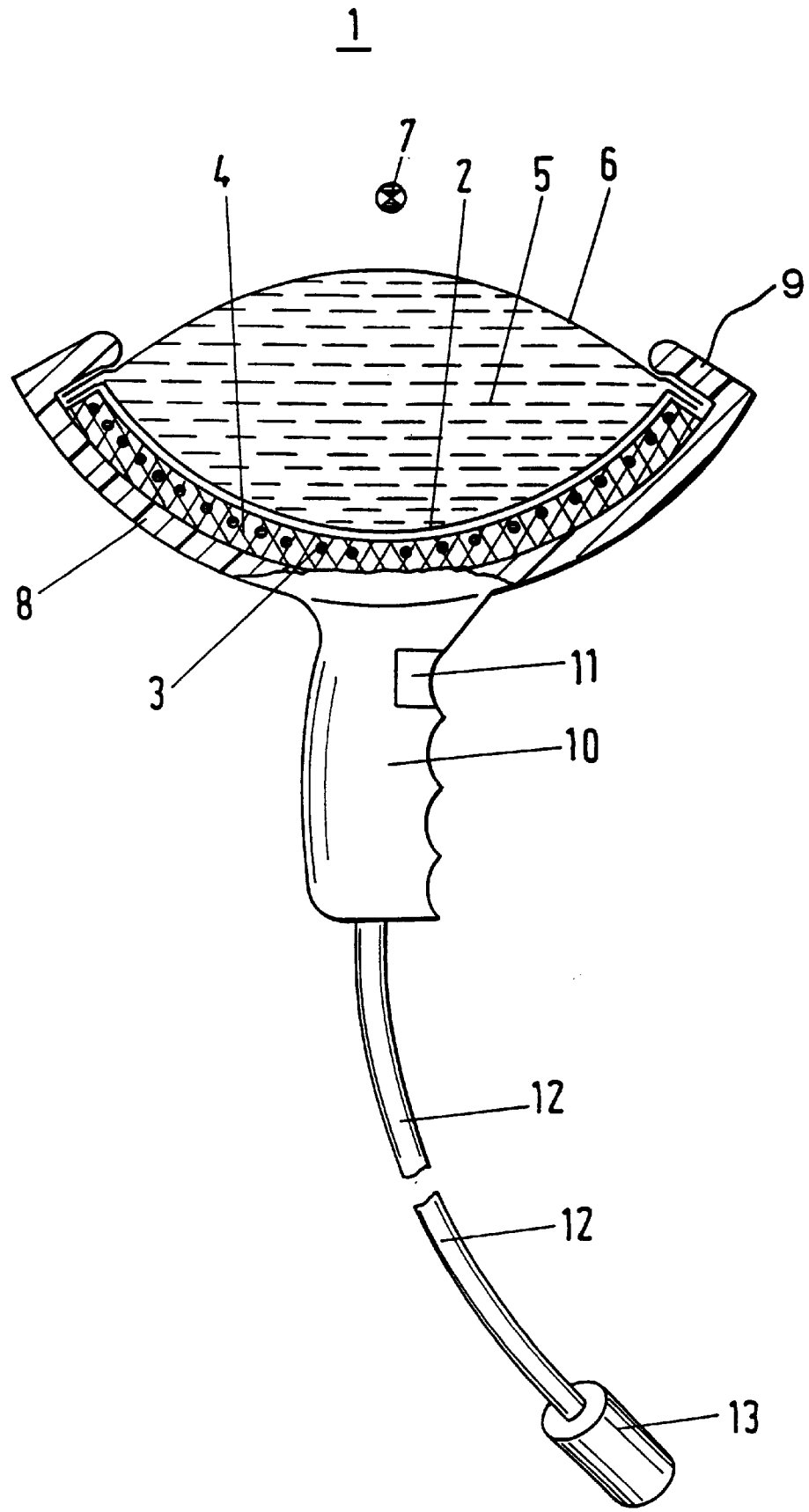

5,941,838

SHOCK WAVE SOURCE BASED ON THE ELECTROMAGNETIC PRINCIPLE

FIELD OF THE INVENTION

The present application is a continuation-in-part application of application Ser. No. 08/873,428 filed Jun. 12, 1997 now abandoned.

The present invention pertains to a shock wave source based on the electromagnetic principle with defined focusing, especially a hand-held therapy head, with an electrically conductive, three-dimensionally curved membrane, with a coil, which is located adjacent to same and to which current pulses can be admitted, with a switchable electric connection means between the coil and an electric power supply unit, with a housing, which accommodates the membrane and a coil embedded in a coil form absorbing a defined compressive stress, with the coil form being located in space between the housing and the membrane, as well as with a transmission medium, which borders on the membrane and exerts pressure on same.

BACKGROUND OF THE INVENTION

In electromagnetic shock wave systems of spherical or other geometry, efficiency depends mostly on the electromagnetic coupling from the exciting coil to the conductive membrane. Good coupling, i.e., adaptation of the membrane to the windings of the coil, is achieved in prior-art systems by overpressure from the membrane or by vacuum in the intermediate space between the coil and the membrane. The technical effort needed to build up, maintain and monitor this vacuum or overpressure is correspondingly great and it increases the manufacturing costs as well as the weight and the volume of the shock wave source.

A shock wave source of this class has been known from a first exemplary embodiment according to DE 33 12 014 A1. A second exemplary embodiment has a rubber- or gel-like transmission medium.

A shock wave source with defined focusing, in which the coil is wound from an electrically conductive wire of rectangular cross section in order to obtain a smooth coil surface with constant, short distance from the membrane and thereby to increase the efficiency of the arrangement, has been known from the Japanese publication *Patent Abstracts of Japan,* JP 1-317 431 (A), Sect. C-697, Mar. 6, 1990, Vol. 14, No. 118.

DE 36 34 378 A1 describes an electromagnetic shock wave source with two coils, which are arranged in parallel and congruently, and which both attract and repel each other due to current flow in the same direction or in opposite directions. One coil is relatively immobile (is rigidly connected to the housing), and the other is relatively easily movable (it is connected to a membrane). The arrangement is to make possible the generation of shock (pressure) and vacuum waves.

An electromagnetic shock wave source, which has a flexible membrane specifically covered with a plurality of small, electrically conductive plates, has been known from EP 0 298 334 A1. The shape of the shock waves can be locally influenced in a specific manner via the inertia of masses and the conductivity of the small plates, unlike in a usual, homogeneous metallic membrane.

A prior-art shock wave source is also described in, e.g., DE-PS 34 43 295. One design, according to FIG. 1 of that publication, uses as the transmission medium a liquid, e.g., water or a liquid halogenated hydrocarbon, which is under static overpressure and it presses as a result the metallic membrane against the dome-shaped coil supported in the housing via a thin insulating layer.

The other design, according to FIG. 2 of the above noted publication, uses as the transmission medium in front of the diaphragm a rubber-elastic solid, which is also under static overpressure and thus presses the membrane. This is achieved here due to the installation of the rubber-elastic body in the compressed state rather than by an external pressure source. This requires a construction which maintains the elastic solid under pressure over a large part of its surface with stable walls. Some drawbacks are to be expected in terms of weight and volume. In addition, the transmission of the shock waves by the elastic body is, in general, not so efficient as, e.g., by a liquid.

SUMMARY AND OBJECTS OF THE INVENTION

In contrast, the basic object of the present invention is to provide a shock wave source based on the electromagnetic principle with defined focusing, especially a hand-held therapy head, with a coil that is arranged in a coil form and is located between a housing and a membrane and with a transmission medium, which shock wave source is characterized by high efficiency and easy handling despite low manufacturing costs.

According to the invention, a shock wave source based on the electromagnetic principle with defined focusing is provided. The shock wave source is especially a hand-held therapy head, with an, electrically conductive, three-dimensionally curved membrane and a coil. The coil is located adjacent to the membrane. Current pulses can be admitted to the coil with a switchable electric connection provided between the coil and an electric power supply unit. A housing is provided, which accommodates the membrane and the coil. The coil is embedded in a coil form which absorbing a defined compressive stress. The coil form is located in space between the housing and the membrane. A transmission medium is provided, which borders on the membrane. The coil form is made deformable and elastically compressible, and the coil form is installed in the compressed state. The installed amount of the transmission medium remains unaffected, or substantially constant, in the operating state after the shock wave source has been assembled and during operation of the shock wave source.

The coil is embedded in a compressible and also otherwise elastically deformable coil form, which is installed in the compressed state, exerting defined compressive stresses or forces on the membrane between it and the housing. The membrane and the housing are usually rigid enough to withstand this pressure without relevant deformations. It is clear to the person skilled in the art that the coil should be arranged as close to the surface of the coil form facing the membrane as possible, taking into account a still sufficient deformation capacity and insulating action of this support area that is in contact with the membrane. Very good electromagnetic coupling is thus achieved between the coil and the membrane as a consequence of the close, uniform mechanical adaptation, without any appreciable extra effort in terms of weight and volume. Pneumatic or hydraulic subsystems for generating the overpressure or vacuum and for pressure monitoring and control are not necessary. The elastic coil form adapts itself to varying radii of curvature within relatively broad limits and it can therefore be used for shock wave therapy heads for various therapeutic purposes.

The coil form is preferably a flat, disk-shaped component of constant thickness. The coil is arranged therein in the undeformed state as manufactured. The membrane may be designed as a deep-drawn, dome-shaped metallic part. A wall limiting the liquid or gel-like transmission medium to the outside may advantageously be designed as a protective film or bellows. The housing is designed as a hard plastic part with a grip made in one piece with it and with an integrated release button, preferably as an injection-molded part.

The coil form, the membrane, and the wall limiting the transmission medium to the outside are held in the housing in a positive-locking and detachable manner.

The present invention will be explained in greater detail below on the basis of the drawing.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawing:

The only figure is a simplified, not true-to-scale partial sectional view and top view of a shock wave source according to the invention.

DESCRIPTION OF THE PREFERRED EMBODIMENT

The shock wave source 1 shown is a hand-held therapy head with short focal distance (focus 7), which is suitable mainly for near-surface use (orthopedics) rather than for deep lithotripsy. The housing 8 of the shock wave source 1 is provided with a grip 10. A switchable electric connection means is provided in the form of a release button 11 for activation of the shock wave source. The electrical connection means also includes a cable 12 indicated with plug 13 connected, or connectable, to an electric power supply unit, not shown, for providing power to a coil 3.

The principal functional elements of the shock wave source 1 are the dome-shaped, electrically conductive membrane 2 and the coil 3, which is embedded in an elastic coil form 4. A transmission medium 5, preferably water or gel, is in mechanical contact with the membrane 2, and is limited to the outside, i.e., toward the patient, by a shock wave-conducting wall 6. The shock wave-conducting wall 6 may be an elastic protective film or an elastic bellows with defined, flexible areas. The elements 2, 4 and 6 are fixed in the housing 8 by means of its circular edge 9 in a positive-locking manner. The switchable electrical connection is provided connected to the coil 3 and the power supply unit.

It shall be pointed out that the elements 2, 4, 6, and 9 are shown in the figure at closely spaced locations from one another for reasons of recognizability and clarity. However, in reality, the membrane 2 is in contact with the coil form 4 over its entire surface, and the edge areas of the membrane 2 and of the wall 6 used for fastening are in contact with one another as well as with the housing edge 9 and the coil form 4. The membrane 2 is connected to the housing 8 in a position, and formed of a material, to compress the coil form 4. The membrane 2 has means for withstanding the compressive force exerted by the coil form 4 and transfers this compressive force to the housing 8. The internal compressive force in this structure is in the range of 10–20 Newtons. The necessary amount of stiffness required in the membrane 2 is not contradictory to its operation because the preferred displacement is so small, in the range of micrometers, that compressive forces within the membrane 2 can be neglected. As was mentioned several times before, the coil form 4 is enclosed in the elastically compressed state between the membrane 2 and the housing 8, as a result of which an especially good mechanical and electromagnetic coupling with the membrane 2 is achieved. This results in a highly conductive and lightweight membrane to achieve maximum acceleration while the transient force, which is given by the electrical parameters, is acting. The current to generate the pulse has the duration of a few microseconds.

The membrane is preferably made of an aluminum alloy of tensile strength of about 300 MPa and a thickness of 0.2–0.3 mm. The coil is preferably a flat coil wound of Kapton insulated copper wire having a wire diameter of 1 mm, and coil diameter of 100–200 mm. The coil is embedded in the coil form 4 formed of an elastic compound; e.g. silicon based elastomers of shore A hardness in the range of 30–60. The thickness of the coil form is preferably in the range of 5–10 mm.

The stiff membrane 2 and elastic coil form 4 are held in place by pressing the edge of the membrane 2 into a groove of the preformed and stiff housing which is preferably an injection molded plastic part. In this manner, the elastic coil form 4 is clamped in between the stiff metallic membrane 2 and the stiff plastic housing 8. An integral part of this housing can be the handpiece.

It is favorable to manufacture the coil form 4 as a flat, disk-shaped component of constant thickness with a flat coil. A coil form created in this manner creates a bias force when inserted into the head in a curved position. This bias force cooperates with the membrane 2 for the mechanical and electromagnetic coupling of the membrane 2 and the coil 3. Part of the compressive force from the membrane is used to transform the elastic coil form 4 from a flat shape to a spherical shape. Preferably about a quarter of the compressive force from the membrane 2 is used for this purpose. Such a coil form 4 can be inserted into, and shaped to fit in, various therapy heads with different focal distances due to elastic arching and compression.

The housing 8 of the shock wave source 1 is preferably manufactured as an injection-molded part from a hard plastic, optionally with fiber reinforcement, which makes it possible to obtain a lightweight and dimensionally stable design. The elements 2, 4 and 6 can be clipped into the finished housing 8 later. However, they may also be placed into the mold already at the time of the injection molding, and the wall 6 may also be installed later, after filling with water or gel. It should finally be noted that details, such as the housing edge 9, the edges of the elements 2, 4 and 6, etc., are shown in the figure in an excessively large size for optical reasons. The person skilled in the art is familiar with the actual dimensions and relations.

While a specific embodiment of the invention has been shown and described in detail to illustrate the application of the principles of the invention, it will be understood that the invention may be embodied otherwise without departing from such principles.

What is claimed is:

1. A shock wave source based on electromagnetic principles with defined focusing, the shock wave source comprising:

an electrically conductive, three-dimensionally curved membrane;

a coil located adjacent to said membrane for admitting current pulses to said membrane;

a switchable electrical connection connected to said coil;

a housing accommodating said membrane;

a coil form, said coil being embedded in said coil form, said coil form absorbing a defined compressive stress, said coil form being located in a space between said housing and said membrane;

a transmission medium which borders on said membrane and exerts pressure on said membrane, said coil form being deformable and elastically compressible, and said coil form being installed in a compressed state, and an installed amount of said transmission medium remains constant in an operating state of the shock wave source.

2. The shock wave source in accordance with claim 1, wherein said coil form is formed as a flat, disk-shaped component of constant thickness with said coil arranged therein in an undeformed state, and said coil is deformed into conformance with said membrane.

3. The shock wave source in accordance with claim 1, wherein said membrane is a deep-drawn, dome-shaped metallic part.

4. The shock wave source in accordance with claim 1, further comprising: a wall limiting said transmission medium at a side of said transmission medium diametrically opposite said membrane.

5. The shock wave source in accordance with claim 4, wherein said transmission medium is one of a liquid substance and gel-like substance, and said wall is one of a protective film and bellows.

6. The shock wave source in accordance with claim 1, wherein:

said housing is a hard plastic part with a grip made in one piece with said housing;

said switchable connection includes an release button integrated with said housing.

7. The shock wave source in accordance with claim 6, wherein said housing is an injection-molded part.

8. The shock wave source in accordance with claim 4, wherein said coil form, said membrane, and said wall have means for being held in said housing in a positive-locking and detachable manner.

9. The shock wave source in accordance with claim 1, wherein said housing is shaped as a hand-held therapy head.

10. An electromagnetic shock wave source with defined focusing, the shock wave source comprising:

an electrically conductive, curved membrane;

a coil located adjacent to said membrane for admitting current pulses to said membrane;

a switchable electrical connection for providing power to said coil;

a housing accommodating said membrane;

a coil form, said coil being embedded in said coil form with said coil absorbing a compressive force, said coil form being located in a space between said housing and said membrane;

a transmission medium which borders on said membrane, said coil form being deformable and elastically compressible, and said coil form being installed in a compressed state, and an amount of said transmission medium remains substantially constant during operation of the shock wave source.

11. The shock wave source in accordance with claim 10, wherein said coil form is a flat, disk-shaped component of constant thickness with said coil arranged therein in an uncompressed state, and said coil is deformed into conformance with said membrane.

12. The shock wave source in accordance with claim 10, wherein said membrane is a dome-shaped metallic part.

13. The shock wave source in accordance with claim 10, further comprising: a wall limiting said transmission medium at a side of said transmission medium diametrically opposite said membrane.

14. The shock wave source in accordance with claim 13, wherein said transmission medium is one of a liquid substance and gel-like substance, and said wall is one of a protective film and bellows.

15. The shock wave source in accordance with claim 10, wherein said coil form, said membrane, and said wall include means for being held in said housing in a positive-locking and detachable manner.

16. The shock wave source in accordance with claim 10, wherein:

said coil form includes means for exerting pressure on said membrane.

17. An electromagnetic shock wave source comprising:

a housing;

an electrically conductive curved membrane connected to said housing;

a coil form being formed of deformable and compressible material, said coil form being positioned between said housing and said membrane in a compressed state;

a coil positioned in said coil form and located adjacent to said membrane;

a switchable electrical connection for providing power to said coil;

a transmission medium positioned adjacent said membrane, an amount of said transmission medium remaining substantially constant during operation of the shock wave source.

18. An electromagnetic shock wave source in accordance with claim 17, wherein:

said coil form is a flat disk-shaped component of constant thickness in an uncompressed state, said membrane is positioned and has means for deflecting said coil form in conformance to said membrane.

19. An electromagnetic shock wave source in accordance with claim 17, wherein:

said membrane is a deep-drawn, dome-shaped metallic part and is biased against said coil form to place said coil form in said compressed state.

20. An electromagnetic shock wave source in accordance with claim 17, wherein:

said transmission medium is one of a liquid substance and gel-like substance;

a wall is provided on a side of said transmission medium diametrically opposite said membrane, said wall is one of a protective film and bellows, and holds said transmission medium against said membrane.

* * * * *